(12) United States Patent
Moffitt et al.

(10) Patent No.: US 10,357,657 B2
(45) Date of Patent: Jul. 23, 2019

(54) SYSTEMS, DEVICES, AND METHODS FOR ELECTRICAL STIMULATION USING FEEDBACK TO ADJUST STIMULATION PARAMETERS

(71) Applicant: Boston Scientific Neuromodulation Corporation, Valencia, CA (US)

(72) Inventors: Michael A. Moffitt, Saugus, CA (US); Sridhar Kothandaraman, Valencia, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 0 days.

(21) Appl. No.: 15/955,407

(22) Filed: Apr. 17, 2018

(65) Prior Publication Data

US 2018/0236238 A1  Aug. 23, 2018

Related U.S. Application Data

(62) Division of application No. 14/876,708, filed on Oct. 6, 2015, now Pat. No. 9,974,959.

(Continued)

(51) Int. Cl.
*A61N 1/05* (2006.01)
*A61N 1/36* (2006.01)
*A61N 1/372* (2006.01)

(52) U.S. Cl.
CPC .......... *A61N 1/36139* (2013.01); *A61N 1/05* (2013.01); *A61N 1/37235* (2013.01)

(58) Field of Classification Search
CPC . A61N 1/36185; A61N 1/0551; A61N 1/3605

(Continued)

(56) References Cited

U.S. PATENT DOCUMENTS 3,999,555 A  12/1976  Person
4,144,889 A  3/1979  Tyers et al.
(Continued)

FOREIGN PATENT DOCUMENTS

EP  0813889  12/1997
EP  1048320  11/2000
(Continued)

OTHER PUBLICATIONS

Zhang, Y., et al., "Atlas-guided tract reconstruction for automated and comprehensive examination of the white matter anatomy," Neuroimage 52(4) (2010), pp. 1289-1301.
(Continued)

*Primary Examiner* — Amanda K Hulbert
*Assistant Examiner* — Philip C Edwards
(74) *Attorney, Agent, or Firm* — Lowe Graham Jones PLLC; Bruce E. Black

(57) ABSTRACT

An electrical stimulation system includes a control module that provides electrical stimulation signals to an electrical stimulation lead coupled to the control module for stimulation of patient tissue. The system also includes a sensor to be disposed on or within the body of the patient and to measure a biosignal; and a processor to communicate with the sensor to receive the biosignal and to generate an adjustment to one or more of the stimulation parameters based on the biosignal. The adjustment can be configured and arranged to steer the electrical stimulation signals to stimulate a region of the patient tissue that is different, at least in part, from a region of the patient tissue stimulated prior to the adjustment. Alternatively or additionally, the biosignal is indicative of a particular patient activity and the adjustment is a predetermined adjustment selected for the particular patient activity.

20 Claims, 10 Drawing Sheets

Related U.S. Application Data

(60) Provisional application No. 62/061,069, filed on Oct. 7, 2014.

(58) Field of Classification Search
USPC .......................................................... 607/45
See application file for complete search history.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulmann |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | DiLorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |

(56) References Cited

U.S. PATENT DOCUMENTS

| | | |
|---|---|---|
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0193231 A1 | 9/2004 | David et al. |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0179557 A1 | 8/2007 | Maschino et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |

(56) References Cited

U.S. PATENT DOCUMENTS

| | | |
|---|---|---|
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215101 A1 | 9/2008 | Rezai et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0163975 A1 | 6/2009 | Gerber et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010387 A1 | 1/2010 | Skelton et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0057161 A1 | 3/2010 | Machado et al. |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0211135 A1* | 8/2010 | Caparso ............... A61N 1/025 |
| | | 607/62 |
| 2010/0324410 A1 | 12/2010 | Paek et al. |
| 2010/0331883 A1 | 12/2010 | Schmitz et al. |
| 2011/0040351 A1 | 2/2011 | Butson et al. |
| 2011/0066407 A1 | 3/2011 | Butson et al. |
| 2011/0137372 A1 | 6/2011 | Makous et al. |
| 2011/0160796 A1 | 6/2011 | Lane et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0224665 A1 | 9/2011 | Crosby et al. |
| 2011/0251583 A1 | 10/2011 | Miyazawa et al. |
| 2011/0270348 A1 | 11/2011 | Goetz |
| 2011/0306845 A1 | 12/2011 | Osorio |
| 2011/0306846 A1 | 12/2011 | Osorio |
| 2011/0307032 A1 | 12/2011 | Goetz et al. |
| 2012/0027272 A1 | 2/2012 | Akinyemi et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0277833 A1 | 11/2012 | Gerber et al. |
| 2012/0302912 A1 | 11/2012 | Moffitt et al. |
| 2012/0303087 A1 | 11/2012 | Moffitt et al. |
| 2012/0303098 A1 | 11/2012 | Perryman |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1166819 | 1/2002 |
| EP | 13272780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |

(56) References Cited

FOREIGN PATENT DOCUMENTS

| WO | 2007/112061 | 10/2007 |
|---|---|---|
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

"BioPSE" The Biomedical Problem Solving Environment, htt12:// www.sci.utah.edu/cibc/software/index.html, MCRR Center for Integrative Biomedical Computing,(2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003), 1-13.

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds,"IEEE Transactions an Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2 Jun. 1998, pp. 200-207.

Andrews, R. J., "Neuroprotection trek—the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006).132-8.

Bazin et al., "Free Software Tools for Atlas-based Volumetric Neuroimage Analysis", Proc. SPIE 5747, Medical Imaging 2005: Image Processing, 1824 May 5, 2005.

Back, C. , et al., "Postoperative Monitoring of the Electrical Properties of Tissue and Electrodes in Deep Brain Stimulation", Neuromodulation, 6(4), (Oct. 2003 ),248-253.

Baker, K. B., et al., "Evaluation of specific absorption rate as a dosimeter of MRI-related implant heating", J Magn Reson Imaging., 20(2), (Aug. 2004),315-20.

Brown, J. "Motor Cortex Stimulation," Neurosurgical Focus ( Sep. 15, 2001) 11(3):E5.

Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.

Cesselin, F. "Opioid and anti-opioid peptides," Fundamental and Clinical Pharmacology (1995) 9(5): 409-33 (Abstract only).

Rezai et al., "Deep Brain Stimulation for Chronic Pain" Surgical Management of Pain, Chapter 44 pp. 565-576 (2002).

Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102(5) pp. 363-367 May 1993.

Bedard, C. , et al., "Modeling extracellular field potentials and the frequency-filtering properties of extracellular space", Biophys J .. 86(3). (Mar. 2004), 1829-42.

Benabid, A. L., et al., "Future prospects of brain stimulation", Neurol Res.;22(3), (Apr. 2000),237-46.

Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005), 196-197.

Mcintyre, Cameron C., et al., "Cellular effects of deep brain stimulation: model-based analysis of activation and inhibition," J Neurophysiol, 91(4) (Apr. 2004), pp. 1457-1469.

Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.

Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.

Butson, C. R., et al., "Deep brainstimulation interactive visualization system", Society for Neuroscience vol. 898.7 (2005).

Hodaie, M., et al., "Chronic anterior thalamus stimulation for intractable epilepsy," Epilepsia, 43(6) (Jun. 2002), pp. 603-608.

Hoekema, R., et al., "Multigrid solution of the potential field in modeling electrical nerve stimulation," Comput Biomed Res., 31(5) (Oct. 1998), pp. 348-362.

Holsheimer, J., et al., "Identification of the target neuronal elements in electrical deep brain stimulation," Eur J Neurosci., 12(12) (Dec. 2000), pp. 4573-4577.

Jezernik, S., et al., "Neural network classification of nerve activity recorded in a mixed nerve," Neurol Res., 23(5) (Jul. 2001), pp. 429-434.

Jones, DK., et al., "Optimal strategies for measuring diffusion in anisotropic systems by magnetic resonance imaging," Magn. Reson. Med., 42(3) (Sep. 1999), pp. 515-525.

Krack, P., et al., "Postoperative management of subthalamic nucleus stimulation for Parkinson's disease," Mov. Disord., vol. 17(suppl 3) (2002), pp. 188-197.

Le Bihan, D., et al., "Diffusion tensor imaging: concepts and applications," J Magn Reson Imaging, 13(4) (Apr. 2001), pp. 534-546.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Levy, AL., et al., "An Internet-connected, patient-specific, deformable brain atlas integrated into a surgical navigation system," J Digit Imaging, 10(3 Suppl 1) (Aug. 1997), pp. 231-237.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Extracellular stimulation of central neurons: influence of stimulus waveform and frequency on neuronal output," J. Neurophysiol., 88(4), (Oct. 2002), pp. 1592-1604.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, Cameron C., et al., "Model-based Analysis of deep brain stimulation of the thalamus," Proceedings of the Second joint EMBS/BM ES Conference, vol. 3, Annual Fall Meeting of the

(56) References Cited

OTHER PUBLICATIONS

Biomedical Engineering Society (Cal. No. 02CH37392) IEEEPiscataway, NJ (2002), pp. 2047-2048.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999); p. 384.

Mcintyre, Cameron C., et al., "Modeling the excitability of mammalian nerve fibers: influence of aflerpotentials on the recovery cycle," J Neurophysiol, 87(2) (Feb. 2002), pp. 995-1006.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59(5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Newak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys., 29(4) (Dec. 1967), pp. 657-664.

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

SI. Jean, P., et al., "Automated atlas integration and interactive three-dimentional visualization tools for planning and guidance in functional neurosurgery," IEEE Transactions on Medical Imaging, 17(5) (1998), pp. 672-680.

Starr, P.A., et al., "Implantation of deep brain simulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk. J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

(56) References Cited

OTHER PUBLICATIONS

Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu. Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R, et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul. 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atlas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic precedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11. Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery" IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

(56) References Cited

OTHER PUBLICATIONS

Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science. 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza. "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.

(56) References Cited

OTHER PUBLICATIONS

An, et al., "Prefronlal cortical projections to longitudinal columns in the midbrain periaqueductal gray in macaque monkeys," J Comp Neural 401 (4) (1998), pp. 455-479.

Bulson, C. R., et al., "Tissue and electrode capacitance reduce neural activation volumes during deep brain stimulation," Clinical Neurophysiology, vol. 116 (2005), pp. 2490-2500.

Carmichael, S. T., et al., "Connectional networks within the orbital and medial prefronlal cortex of macaque monkeys," J Comp Neural 371 (2) (1996), pp. 179-207.

Croxson, et al., "Quantitative investigation of connections of the prefronlal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol Psychiatry 15 (1) (2010), pp. 64-79.

Greenberg. et al., "Three-year outcomes in deep brain stimulation for highly resistant obsessive-compulsive disorder," Neuropsychopharmacology 31 (11) (2006), pp. 2384-2393.

Gutman et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and Iimbic circuits that are affected by deep brain stimulation," Front Biosci 14 (2009), pp. 1823-1834.

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Funel. Neurosurg. 87(2009), pp. 229-240.

Machado. et al., "Functional topography of the ventral striatum and anterior limb of the internal capsule determined by electrical stimulation of awake patients," Clin Neurophysiol 120 (11) (2009), pp. 1941-1948.

Malone, et al., "Deep brain stimulation of the ventral capsule/ventral striatum for treatment-resistant depression," Biol Psychiatry 65 (4) (2009), pp. 267-275.

Mayberg, H. S., et al., "Deep brain stimulation for treatment-resistant depression," Neuron, 45(5) (Mar. 3, 2005), pp. 651-660.

Mayberg, H. S., et al., "Limbic-cortical dysregulation: a proposed model of depression," J Neuropsychiatry Clin Neurosci. 9 (3) (1997), pp. 471-481.

McIntyre,C. C., et al., "Network perspectives on the mechanisms of deep brain stimulation," Neurobiol Dis 38 (3) (2010), pp. 329-337.

Miocinovic, S., et al., "Experimental and theoretical characterization of the voltage distribution generated by deep brain stimulation," Exp Neurol 216 (i) (2009), pp. 166-176.

Nuttin, et al., "Electrical stimulation in anterior limbs of internal capsules in patients with obsessive-compulsive disorder," Lancet 354 (9189) (1999), p. 1526.

Saxena, et al., "Cerebral glucose metabolism in obsessive-compulsive hoarding," Am J Psychiatry. 161 (6) (2004), pp. 1038-1048.

Viola, et al., "Importance-driven focus of attention," IEEE Trans Vis Comput Graph 12 (5) (2006), pp. 933-940.

Wakana, S., et al., "Reproducibility of quantitative tractography metheds applied to cerebral white matter," Neuroimage 36 (3) (2007), pp. 536-544.

Mayr et al., "Basic Design and Construction of the Vienna FES Implants: Existing Solutions and Prospects for New Generations of Implants", Medical Engineering & Physics, 2001; 23:53-60.

Nowinski, W. L., et al., "Statistical analysis of 168 bilateral subthalamic nucleus implantations by means of the probabilistic functional atlas.", Neurosurgery 57(4 Suppl) (Oct. 2005),319-30.

Obeso, J. A., et al., "Deep-brain stimulation of the subthalamic nucleus or the pars interna of the globus pallidus in Parkinson's disease.", N Engl J Med., 345(13). The Deep-Brain Stimulation for Parkinson's Disease Study Group, (Sep. 27, 2001 ),956-63.

Butson et al., "Current Steering to control the volume of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nana to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medicai Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work! Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based; Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in improving contralateral parkinsonism.", Brain 129(Pt 7) (Jul. 2006), 1732-4 7.

Rattay, F, "Analysis of models for external stimulation of axons", IEEE Trans. Biomed. Eng. vol. 33 (1986),974-977.

(56) References Cited

OTHER PUBLICATIONS

Rattay, F., "Analysis of the electrical excitation of CNS neurons", IEEE Transactions on Biomedical Engineering 45(6). (Jun. 1998),766-772.

Rose, T. L., et al., "Electrical stimulation with Pt electrodes. VIII. Electrochemically safe charge injection limits with 0.2 ms pulses [neuronal application]". IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl. 191, (Sep. 2003), 14-9.

Schwan, H.P., et al., "The conductivity of living tissues", Ann NY Acad Sci., 65(6). (Aug. 1957), 1007-13.

Taylor, R. S., et a., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 45, No. 3, Jul. 2009, pp. 786-802.

Geddes, L. A., et al., "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments-electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Izad, Oliver, "Computationally Efficient Method in Predicating Axonal Excitation," Dissertation for Master Degree, Department of Biomedical Engineering, Case Western Reserve University, May 2009.

Jaccard, Paul, "Elude comparative de la distribution florale dans une portion odes Aples et des Jura," Bulletin de la Societe Vaudoise des Sciences Neturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi:10.1007/BF01908075.

Cover, T.M. et al., "Elements of information theory," (1991) John Wiley & Sons, New York, NY.

Meila, Marina, "Comparing Clusterings by the Variation of Information," Learning Theory and Kernel Machines (2003): 173-187.

Viola, P., et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Introduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al. "Sketching and Composing Widgets for 3D Manipulation," Eurographics, Apr. 2008, vol. 27, No. 2, pp. 301-310.

Volkmann, J. , et al., "Basic algorithms for the programming of deep brain stimulation in Parkinson's disease", Mov Disord., 21 Suppl 14. (Jun. 2006),S284-9.

Walter, B. L., et al., "Surgical treatment for Parkinson's disease", Lancet Neural. 3(12). (Dec. 2004),719-28.

Wei, X. F., et al., "Current density distributions, field distributions and impedance analysis of segmented deep brain stimulation electrodes", J Neural Eng .. 2(4). (Dec. 2005), 139-47.

Zonenshayn, M. , et al., "Location of the active contact within the subthalamic nucleus (STN) in the treatment of idiopathic Parkinson's disease.", Surg Neurol., 62(3) (Sep. 2004),216-25.

Da Silva et al (A primer on diffusion tensor imaging of anatomical substructures. Neurosurg Focus 15(1): p. 1-4, Article 4, 2003.)

Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.

Grill, W. M., "Stimulus waveforms for selective neural stimulation", IEEE Engineering in Medicine and Biology Magazine, 14(4}, (Jul.-Aug. 1995), 375-385.

Miocinovic, S., et al., "Sensitivity of temporal excitation properties to the neuronal element activated by extracellular stimulation", J Neurosci Methods. 132(1). (Jan. 15, 2004), 91-9.

Hunka, K. et al., Nursing Time to Program and Assess Deep Brain Stimulators in Movement Disorder Patients, J. Neursci Nurs., 37: 204-10 (Aug. 2005).

Moss, J. , et al., "Electron microscopy of tissue adherent to explanted electrodes in dystonia and Parkinson's disease", Brain, 127{Pt 12). (Dec. 2004 ),2755-63.

Montgomery, E. B., et al., "Mechanisms of deep brain stimulation and future technical developments.", Neurol Res. 22(3). (Apr. 2000),259-66.

Merrill, D. R., et al., "Electrical stimulation of excitable tissue: design of efficacious and safe protocols", J Neurosci Methods. 141(2), (Feb. 15, 2005), 171-98.

Fisekovic et al., "New Controller for Functional Electrical Stimulation Systems", Med. Eng. Phys. 2001; 23:391-399.

McIntyre, Cameron , et al., "Finite element analysis of the current-density and electric field generated by metal microelectrodes", Ann Biomed Eng . 29(3), (2001 ),227-235.

Foster, K. R., et al., "Dielectric properties of tissues and biological materials: a critical review.", Grit Rev Biomed Ena. 17(1 ), (1989),25-104.

Limousin, P., et al., "Electrical stimulation of the subthalamic nucleus in advanced Parkinson's disease", N Engl J Med .. 339(16), (Oct. 15, 1998), 1105-11.

Kitagawa, M., et al., "Two-year follow-up of chronic stimulation of the posterior subthalamic white matter for tremor-dominant Parkinson's disease.", Neurosurgery. 56(2). (Feb. 2005),281-9.

Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.

Holsheimer, J. , et al., "Chronaxie calculated from current-duration and voltage-duration data", J Neurosci Methods. 97(1). (Apr. 1, 2000),45-50.

Hines, M. L., et al., "The Neuron simulation environment", Neural Comput. 9(6). (Aug. 15, 1997), 1179-209.

Herzog, J., et al., "Most effective stimulation site in subthalamic deep brain stimulation for Parkinson's disease", Mov Disord. 19(9). (Sep. 2004),1050-4.

Hershey, T., et al., "Cortical and subcortical blood flow effects of subthalamic nucleus stimulation in PD.", Neurology 61(6). (Sep. 23, 2003),816-21.

Hemm, S. , et al., "Evolution of Brain Impedance in Dystonic Patients Treated by GPi Electrical Stimulation", Neuromodulation 7(2) (Apr. 2004),67-75.

Hemm, S., et al., "Deep brain stimulation in movement disorders: stereotactic coregistration of two-dimensional electrical field modeling and magnetic resonance imaging.", J Neurosurg. 103(6): (Dec. 2005);949-55.

Haueisen, J, et al., "The influence of brain tissue anisotropy on human EEG and MEG", Neuroimage 15(1) (Jan. 2002),159-166.

(56) References Cited

OTHER PUBLICATIONS

Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T. , et al., "Stimulation of the subthalamic nucleus changes the firing pattern of pallidal neurons", J Neurosci. 23(5). (Mar. 1, 2003),1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
McNaughtan et al., "Electrochemical Issues in Impedance Tomography", 1st World Congress on Industrial Process Tomography, Buxton, Greater Manchester, Apr. 14-17, 1999.
Grill, WM., et al., "Electrical properties of implant encapsulation tissue", Ann Biomed Eng. vol. 22. (1994),23-33.
Grill, W. M., et al., "Deep brain stimulation creates an informational lesion of the stimulated nucleus", Neuroreport. 15I7t (May 19, 2004 ), 1137-40.
International Search Report and Written Opinion for PCT/US2015/054282 dated Jan. 28, 2016.
Official Communication for U.S. Appl. No. 15/004,771 dated Sep. 6, 2017.
Official Communication for U.S. Appl. No. 14/876,708 dated Sep. 5, 2017.
Official Communication for U.S. Appl. No. 14/876,708 dated Dec. 13, 2017.

\* cited by examiner

SYSTEMS, DEVICES, AND METHODS FOR ELECTRICAL STIMULATION USING FEEDBACK TO ADJUST STIMULATION PARAMETERS

CROSS-REFERENCE TO RELATED APPLICATIONS

This application is a divisional of U.S. patent application Ser. No. 14/876,708, filed Oct. 6, 2015, which claims the benefit under 35 U.S.C. § 119(e) of U.S. Provisional Patent Application Ser. No. 62/061,069, filed Oct. 7, 2014, both of which are incorporated herein by reference.

FIELD

The present invention is directed to the area of implantable electrical stimulation systems and methods of making and using the systems. The present invention is also directed to implantable electrical stimulation systems that include devices or methods for electrical stimulation which utilize feedback from one or more sensors to adjust stimulation parameters, as well as methods of making and using the electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation system including an implantable control module for implantation in a body of a patient and having an antenna and a processor coupled to the antenna. (In other embodiments, the control module is an external control module.) The control module provides electrical stimulation signals to an electrical stimulation lead coupled to the implantable control module for stimulation of patient tissue. The system also includes an external programming unit to communicate with the processor of the implantable control module using the antenna and to provide or update stimulation parameters for production of the electrical stimulation signals; a sensor to be disposed on or within the body of the patient and to measure a biosignal; and a biosignal processor to communicate with the sensor to receive the biosignal and to generate an adjustment to one or more of the stimulation parameters based on the biosignal. The adjustment can be configured and arranged to steer the electrical stimulation signals to stimulate a region of the patient tissue that is different, at least in part, from a region of the patient tissue stimulated prior to the adjustment. Alternatively or additionally, the biosignal is indicative of a particular patient activity and the adjustment is a pre-determined adjustment selected for the particular patient activity.

In at least some embodiments, the external programming unit includes the biosignal processor. In at least some embodiments, the biosignal processor is configured and arranged for communication with the external programming unit to deliver the adjustment to the external programming unit. In at least some embodiments, the sensor is disposed on the control module.

In at least some embodiments, the system also includes a lead coupleable to the control module and having electrodes for delivering the electrical stimulation signals to the patient tissue. In at least some embodiments, the sensor is disposed on the lead.

In at least some embodiments, the biosignal processor is configured and arranged to perform the following actions: receive the biosignal from the sensor; and determine the adjustment to one or more stimulation parameters based on the biosignal. In at least some embodiments, the biosignal processor is configured and arranged to perform the additional following action: deliver the adjustment to one of the external programming unit or the control module.

In at least some embodiments, the adjustment is provided to the control module automatically and without user intervention.

Another embodiment is an electrical stimulation system including a sensor to be disposed on or within the body of the patient and to measure a biosignal; and a control module having a processor. The control module provides electrical stimulation signals to an electrical stimulation lead coupled to the control module for stimulation of patient tissue. The processor is configured and arranged to communicate with the sensor to receive the biosignal and to generate an adjustment to one or more of the stimulation parameters based on the biosignal. The adjustment can be configured and arranged to steer the electrical stimulation signals to stimulate a region of the patient tissue that is different, at least in part, from a region of the patient tissue stimulated prior to the adjustment. Alternatively or additionally, the biosignal is indicative of a particular patient activity and the adjustment is a pre-determined adjustment selected for the particular patient activity.

In at least some embodiments, the control module is an implantable control module configured and arranged for implantation in a body of a patient, the implantable control module further comprising an antenna coupled to the processor. In at least some embodiments, the sensor is disposed on the control module. In other embodiments, the control module is an external control module.

In at least some embodiments, the processor is configured and arranged to perform the following actions: receive the biosignal from the sensor; and determine the adjustment to one or more stimulation parameters based on the biosignal.

In at least some embodiments, the system also includes a lead coupleable to the control module and comprising a plurality of electrodes for delivering the electrical stimulation signals to the patient tissue. In at least some embodiments, the sensor is disposed on the lead.

Yet another embodiment is a non-transitory computer-readable medium having processor-executable instructions for adjusting one or more stimulation parameters, the processor-executable instructions when installed onto a device enable the device to perform actions, including: receive a biosignal from one or more sensors; and determine an adjustment to the one or more stimulation parameters based on the biosignal. The adjustment can be configured and arranged to steer the electrical stimulation signals to stimulate a region of the patient tissue that is different, at least in part, from a region of the patient tissue stimulated prior to the adjustment. Alternatively or additionally, the biosignal is indicative of a particular patient activity and the adjustment is a pre-determined adjustment selected for the particular patient activity.

In at least some embodiments, the processor-executable instructions when installed onto a device enable the device to perform the following additional action: deliver the adjustment to one of an external programming unit or a control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
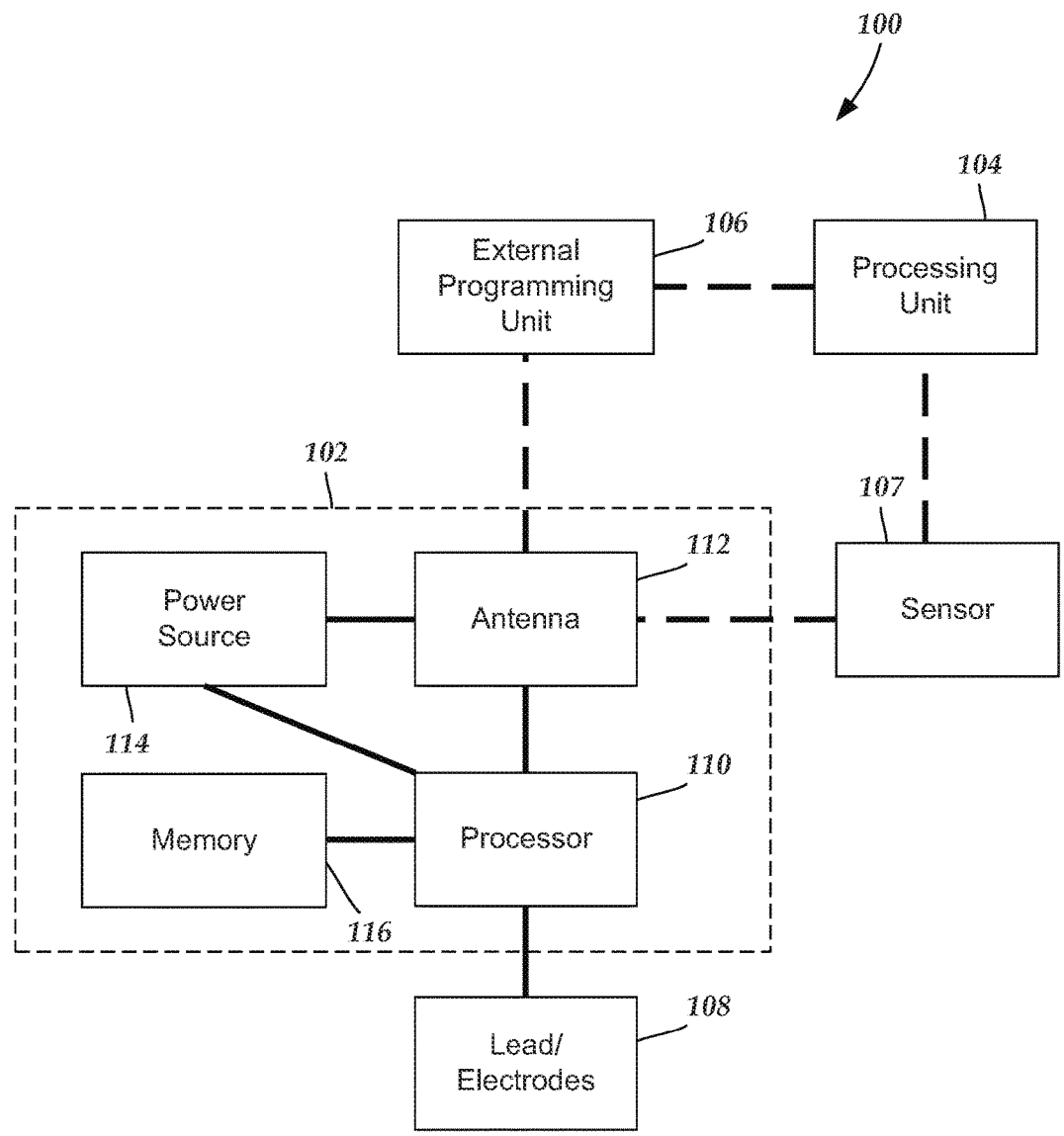
FIG. 1 is a schematic block diagram of one embodiment of an electrical stimulation system, according to the invention.

The present invention is directed to the area of implantable electrical stimulation systems and methods of making and using the systems. The present invention is also directed to implantable electrical stimulation systems that include devices or methods for electrical stimulation which utilize feedback from one or more sensors to adjust stimulation parameters, as well as methods of making and using the electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

An electrical stimulation system can include one or more sensors that can measure a functional response to electrical stimulation treatment. The measurements can be used in an automated or semi-automated manner to alter one or more stimulation parameters to enhance the treatment. In at least some embodiments, the system may perform these measurements under one or more conditions such as, for example, during a programming session; at regular or irregular intervals during operation of the system; or when initiated by a clinician, patient, or other individual.

In at least some embodiments, the electrical stimulation system can have a closed-loop feedback function using the one or more sensors and the respective measurements. The feedback function may be automated or semi-automated. In at least some embodiments, the feedback function may be initiated under one or more conditions such as, for example, during a programming session; at regular or irregular intervals during operation of the system; or when directed by a clinician, patient, or other individual.

In at least some embodiments, the measurements can be used to steer the electrical stimulation (for example, the electrical current). Steering can be performed by, for example, altering the selection of electrode(s) that provide the electrical stimulation; altering the amplitude (or other stimulation parameters such as frequency or duration) of stimulation provided by given electrodes; or the like or any combination thereof. In at least some embodiments, steering of the electrical stimulation can include multiple timing channels which utilize the electrodes of the lead to generate different electric fields. The electric fields for the different timing channels can be interleaved temporally to alter the electrical stimulation of the patient tissue. Stimulation steering can be used to alter the electric field produced by the system and to alter the portion of patient tissue being stimulated or the amount of stimulation provided to a region of patient tissue. This can tailor the stimulation to the patient or to the current condition of the patient. Any combination of these steering methods can also be employed.

In at least some embodiments, one or more sensors can be used to determine patient postural, positional, or activity changes or to determine changes in disease or disorder progression or modality, or changes in the stimulation system. These measurements can be used to alter one or more electrical stimulation parameters. The system may perform these measurements under one or more conditions such as, for example, during a programming session; at regular or irregular intervals during operation of the system; or when directed by a clinician, patient, or other individual. In at least some embodiments, the electrical stimulation system can have a closed-loop feedback function that allows the system to alter stimulation as a result of changes in patient activity, changes in the disease or disorder, or changes to the components of the system or their surroundings.

FIG. 1 illustrates schematically one embodiment of an electrical stimulation system 100 that includes an implantable control module (e.g., an implantable electrical stimulator or implantable pulse generator) 102, one or more leads 108 with electrodes, one or more external programming units 106, one or more sensors 107, and a processing unit 104. Alternatively, the implantable control module 102 can be part of a microstimulator with the electrodes disposed on the housing of the microstimulator. The microstimulator may not include a lead or, in other embodiments, a lead may extend from the microstimulator. As yet another alternative, the control module can be external to the patient. One example of an external control module is an external trial stimulator that can be used temporarily during the implantation procedure to test stimulation using the lead.

It will be understood that the electrical stimulation system can include more, fewer, or different components and can have a variety of different configurations including those configurations disclosed in the references cited herein. For example, although FIG. 1 illustrates one external programming unit 106, one control module 102, and one sensor 107, it will be understood that the system can include more than one external programming unit, more than one control module, more than one sensor, or any combination thereof.

The lead 108 is coupled, or coupleable, to the implantable control module 102. The implantable control module 102 includes a processor 110, an antenna 112 (or other communications arrangement), a power source 114, and a memory 116, as illustrated in FIG. 1.

Figure 2:
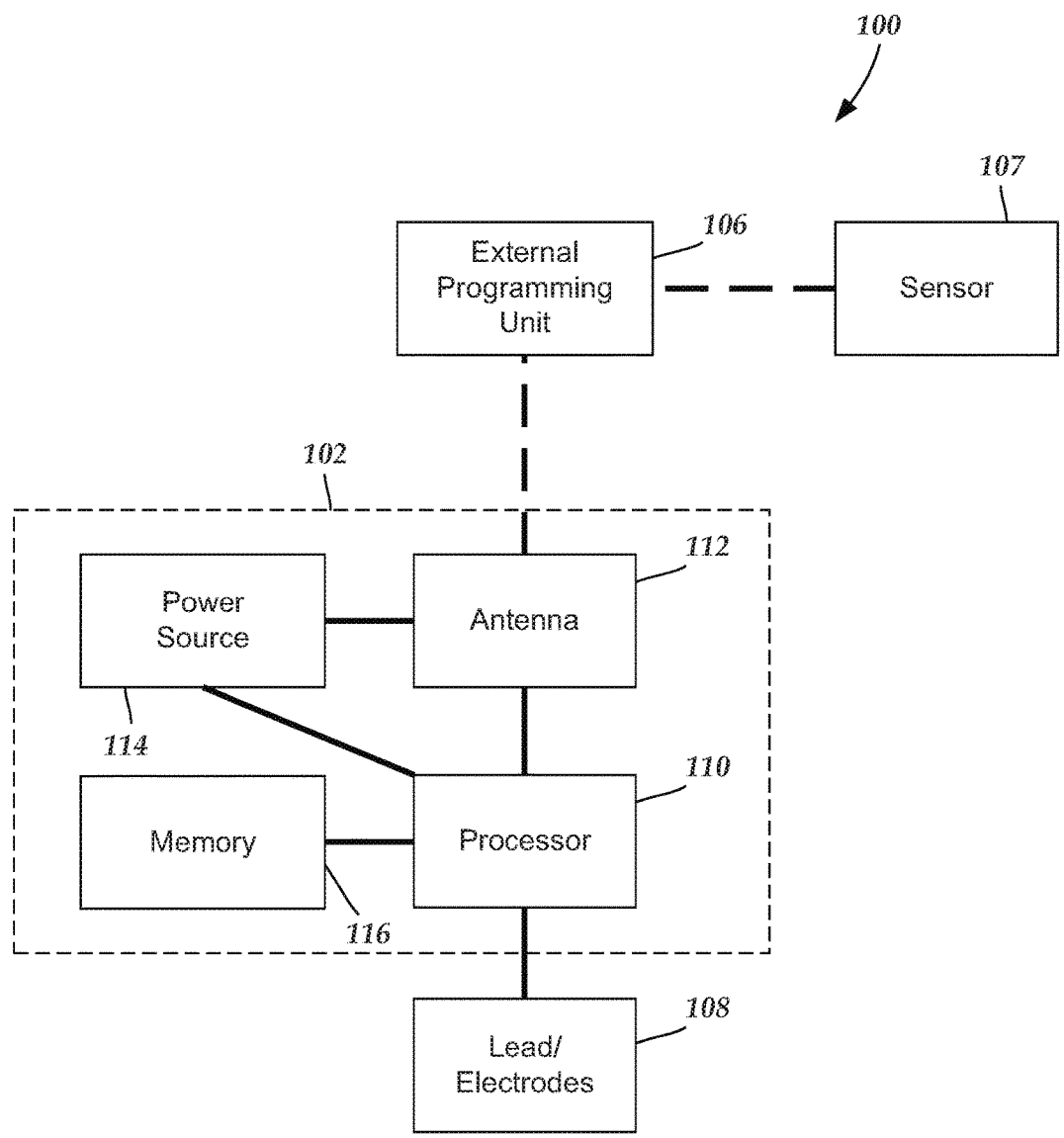
FIG. 2 is a schematic block diagram of another embodiment of an electrical stimulation system, according to the invention.
Figure 3:
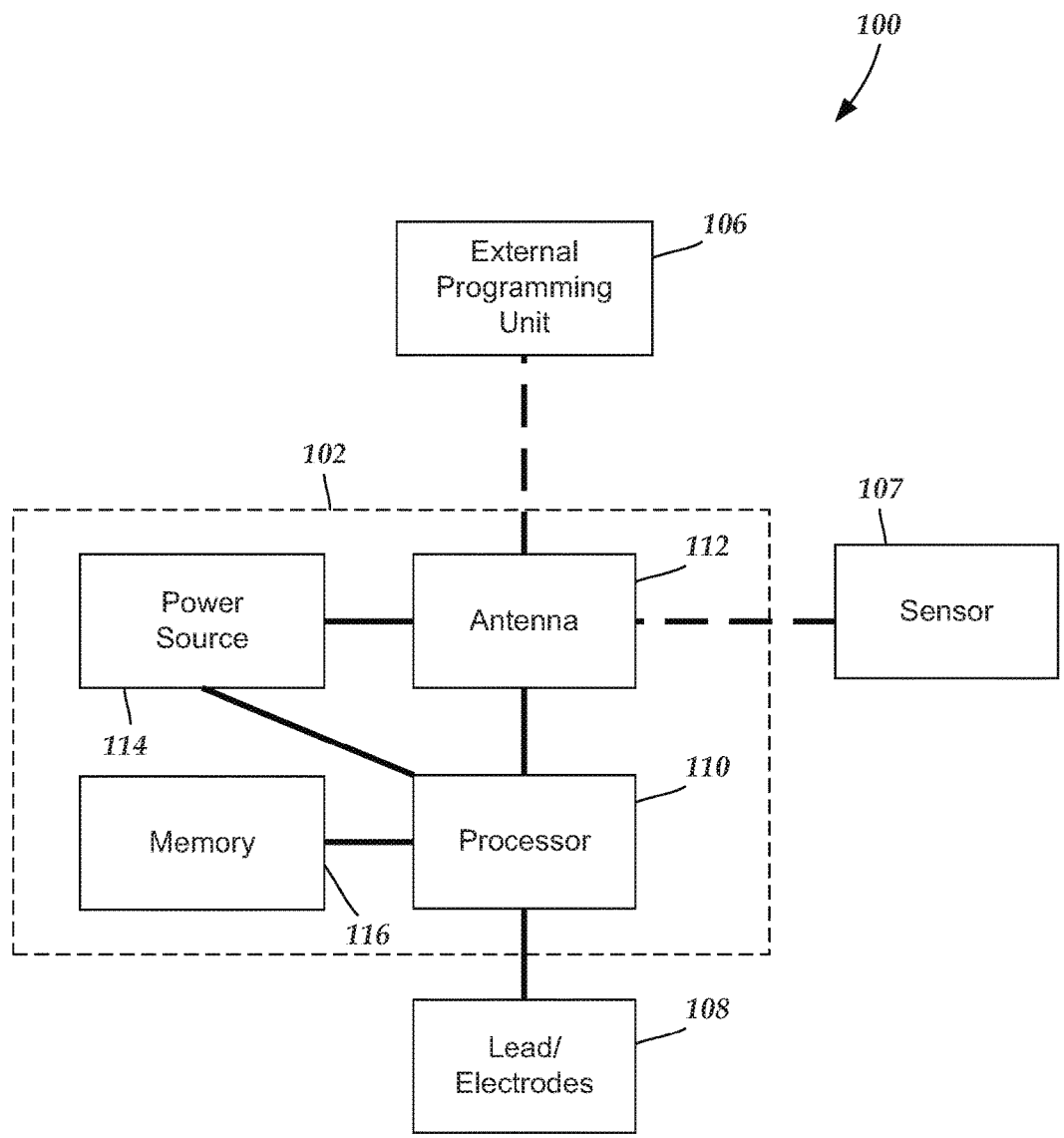
FIG. 3 is a schematic block diagram of another embodiment of an electrical stimulation system, according to the invention.

FIGS. 2 and 3 illustrate other embodiments in which the processing unit is omitted and the external programming unit 106, sensor(s) 107, or control module 102 or any combination thereof can perform the functions of the processing unit. In the embodiment of FIG. 2, the sensor 107 is in communication with the external programming unit 106. In the embodiment of FIG. 3, the sensor 107 is in communication with the control module 102.

Figure 4:
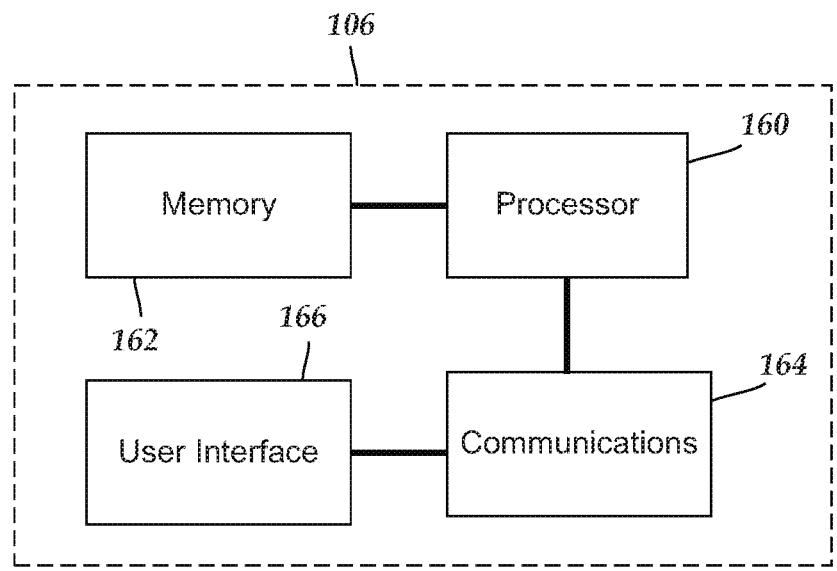
FIG. 4 is a schematic block diagram of one embodiment of an external programming unit, according to the invention.

One example of an external programming unit 106 is illustrated in FIG. 4 and includes a processor 160, a memory 162, a communications arrangement 164 (such as an antenna or any other suitable communications device such as those described below), and a user interface 166. Suitable devices for use as an external programming unit can include, but are not limited to, a computer, a tablet, a mobile telephone, a personal desk assistant, a dedicated device for external programming, remote control, or the like. It will be understood that the external programming unit 106 can include a power supply or receive power from an external source or any combination thereof. The external programming unit 106 can be a home station or unit at a clinician's office or any other suitable device. In some embodiments, the external programming unit 106 can be a device that is worn on the skin of the user or can be carried by the user and can have a form similar to a pager, cellular phone, or remote control, if desired. The external programming unit 106 can be any unit that can provide information to the control module 102. One example of a suitable external programming unit 106 is a computer operated by the clinician or patient to send signals to the control module 102. Another example is a mobile device or an application on a mobile device that can send signals to the control module 102

Figure 5:
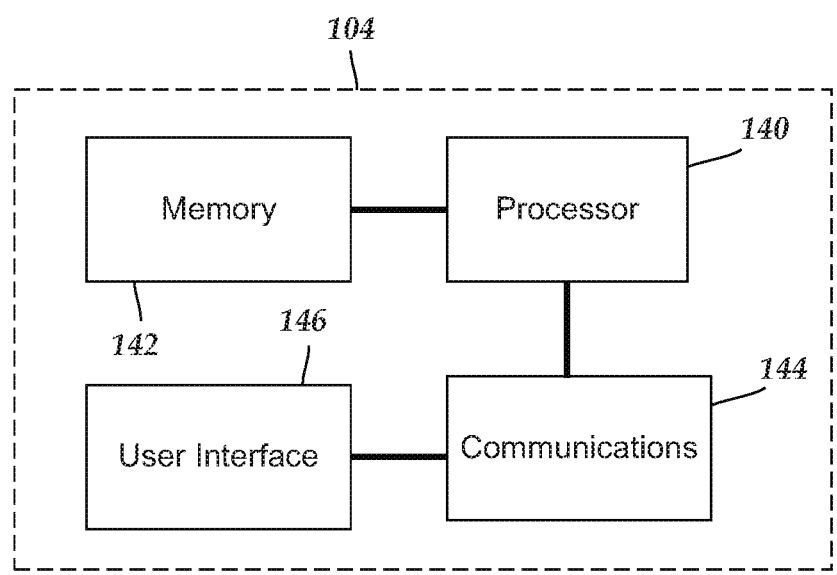
FIG. 5 is a schematic block diagram of one embodiment of a processing unit, according to the invention.

One example of a processing unit 104 is illustrated in FIG. 5 and includes a processor 140, a memory 142, a communications arrangement 144 (such as an antenna or any other suitable communications device such as those described below), and an optional user interface 146. Suitable devices for use as a processing unit can include, but are not limited to, a computer, a tablet, a server or server farm, or the like. It will be understood that the processing unit 104 can include a power supply or receive power from an external source or any combination thereof.

Methods of communication between devices or components of a system can include wired (including, but not limited to, USB, mini/micro USB, HDMI, and the like) or wireless (e.g., RF, optical, infrared, near field communication (NFC), Bluetooth™, or the like) communications methods or any combination thereof. By way of further example, communication methods can be performed using any type of communication media or any combination of communication media including, but not limited to, wired media such as twisted pair, coaxial cable, fiber optics, wave guides, and other wired media and wireless media such as acoustic, RF, optical, infrared, NFC, Bluetooth™ and other wireless media. These communication media can be used for communications units 144, 164 or as antenna 112 or as an alternative or supplement to antenna 112.

Turning to the control module 102, some of the components (for example, a power source 114, an antenna 112, and a processor 110) of the electrical stimulation system can be positioned on one or more circuit boards or similar carriers within a sealed housing of the control module (implantable pulse generator,) if desired. Any power source 114 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the antenna 112 or a secondary antenna. The external power source can be in a device that is mounted on the skin of the user or in a unit that is provided near the user on a permanent or periodic basis.

If the power source 114 is a rechargeable battery, the battery may be recharged using the antenna 112, if desired. Power can be provided to the battery for recharging by inductively coupling the battery through the antenna to a recharging unit external to the user.

A stimulation signal, such as electrical current in the form of electrical pulses, is emitted by the electrodes of the lead 108 (or a microstimulator) to stimulate neurons, nerve fibers, muscle fibers, or other body tissues near the electrical stimulation system. Examples of leads are described in more detail below. The processor 110 is generally included to control the timing and electrical characteristics of the electrical stimulation system. For example, the processor 110 can, if desired, control one or more of the timing, frequency, strength, duration, and waveform of the pulses. In addition, the processor 110 can select which electrodes can be used to provide stimulation, if desired. In some embodiments, the processor 110 selects which electrode(s) are cathodes and which electrode(s) are anodes. In some embodiments, the processor 110 is used to identify which electrodes provide the most useful stimulation of the desired tissue.

With respect to the control module 102, external programming unit 106, and database unit 104, any suitable processor 110, 140, 160 can be used in these devices. For the control module 102, the processor 110 is capable of receiving and interpreting instructions from an external programming unit 106 that, for example, allows modification of pulse characteristics. In the illustrated embodiment, the processor 110 is coupled to the antenna 112. This allows the processor 110 to receive instructions from the external programming unit 106 to, for example, direct the pulse characteristics and the selection of electrodes, if desired. The antenna 112, or any other antenna described herein, can have any suitable configuration including, but not limited to, a coil, looped, or loopless configuration, or the like. In one embodiment, the antenna 112 is capable of receiving signals (e.g., RF signals) from the external programming unit 106 or sensor 107.

The signals sent to the processor 110 via the antenna 112 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the control module 102 to cease operation, to start operation, to start charging the battery, or to stop charging the battery.

Optionally, the control module 102 may include a transmitter (not shown) coupled to the processor 110 and the antenna 112 for transmitting signals back to the external programming unit 106 or another unit capable of receiving the signals. For example, the control module 102 may transmit signals indicating whether the control module 102 is operating properly or not or indicating when the battery needs to be charged or the level of charge remaining in the battery. The processor 110 may also be capable of transmitting information about the pulse characteristics so that a user or clinician can determine or verify the characteristics.

Any suitable memory 116, 142, 162 can be used for the respective components of the system 100. The memory 116, 142, 162 illustrates a type of computer-readable media, namely computer-readable storage media. Computer-readable storage media may include, but is not limited to, nonvolatile, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The user interface 166 of the external programming unit 106 and optional user interface 146 of the processing unit 104 can be, for example, a keyboard, mouse, touch screen, track ball, joystick, voice recognition system, or any combination thereof, and the like. Alternatively or additionally, the user interface 166 of the external programming unit 106 can include one or more microphones, sensors, cameras, or the like to obtain clinician or patient input. For example, the clinician or patient may provide input verbally (e.g. voice command recognition, voice recordings) or visually (e.g. video of patient, non-touch gesture recognition, or the like). In at least some embodiments, patient feedback can be provided by the clinician or other user through the external programming unit 106.

The one or more sensors 107 can be any suitable sensors for measuring a biosignal (which can include a variable biological condition such as, for example, skin resistance, skin or tissue impedance, temperature, or the like). Examples of biosignals include EEG, electrocochleograph (ECOG), electromyography, skin resistance, skin or tissue impedance, muscle tone, heart rate, ECG, blood pressure, electrical signals traversing the spinal cord or a nerve or group of nerves, tremors or other movement (which can be measured using, for example, displacement, velocity, acceleration, direction of movement, and the like), muscle contraction or relaxation, vibration, temperature, breathing, oxygen levels, chemical concentrations, gait, skin tone, or the like.

Any sensor suitable for measuring the corresponding biosignal can be used. The sensor can be a mechanical, electrical, chemical, or biological sensor or any combination thereof. The sensor can be inserted in, implanted in, positioned on, or otherwise coupled to the body of the patient. In some embodiments, at least one sensor is provided on the lead or control module and can be, for example, a separate recording electrode for recording electrical signals or can be one or more stimulating electrodes that also are used for recording electrical signals. In other embodiments, the sensor can be attached to the body of the patient using, for example, a band, cuff, belt, clamp, clip, friction, adhesive, or the like or any combination thereof. In some embodiments, the sensor can be provided on, or attached to, the external programming unit or a patient remote control or a charging unit for the control module.

The sensor 107 can be in communication with the external programming unit 106, the control module 102, the processing unit 104, or any combination thereof. Such communication can be wired or wireless or any combination thereof using any of the communication methods described above. In at least some embodiments, the sensor 107 can include a processor, a memory, or both.

In at least some embodiments, the sensor 107 is deployed and used only during a programming session. In other embodiments, the sensor 107 may be deployed on or within the patient for an extended period of time (for example, at least one day, one week, one month, six months, one year, or longer). In at least some embodiments, the sensor 107 may be in regular or constant communication with the control module 102 or external programming unit 106. In at least some embodiments, the sensor 107 may contact the control module 102, external programming unit 106, or processing unit 104 when requested, when a change in the biosignal exceeds a threshold, at regular or irregular intervals, or any combination thereof.

As an example, in at least some embodiments, the system includes a sensor that detects or measures muscle tremors or rigidity. For example, the sensor can be an accelerometer or the like and can be a fingertip sensor or a sensor disposed on a band, belt, adhesive, or other fastener so that the sensor can be mounted on the leg, arm, or other portion of the patient. Such a sensor could be used, for example, with an electrical stimulation system for treating Parkinson's disease, essential tremor, dystonia, hemiballismus, Tourette's syndrome, Huntington's disease, urge incontinence, or any other disease or disorder that causes muscle tremors or other involuntary muscle actions or rigidity or for treating symptoms such as, for example, tremor, rigidity, bradykinesia, freezing of gait, dyskinesias, or the like.

As another example, in at least some embodiments, the system includes a sensor that detects or measures blood pressure. For example, the sensor can be a cuff or other blood pressure measurement device, such as a fingertip sensor or a sensor disposed on a band, belt, adhesive, or other fastener so that the sensor can be mounted on the leg, arm, or other portion of the patient. Such a sensor could be used, for example, with an electrical stimulation system for carotid sinus stimulation, deep brain stimulation, or the like.

Yet another example, in at least some embodiments, the sensor includes a sensor that detects or measures heart rate and parameters associated heart rate, such as heart rate variability (HR variability). HR variability can be correlated with anxiety or sources that cause anxiety (pain, PTSD, OCD, and the like). Heart Rate is also a surrogate for activity monitoring. In at least some embodiments, the heart rate can be monitored by a sensor disposed on a lead implanted in or near the spinal cord and used for electrical stimulation of the spinal cord.

In at least some embodiments, the system includes a sensor that detects or measures movement. For example, the sensor can be a global positioning sensor (GPS), accelerometer, heart rate or pulse rate monitor, blood pressure cuff or other blood pressure measurement device such as a fingertip sensor, or the like. Such a sensor could be used, for example, with an electrical stimulation system to adjust one or more stimulation parameters based on patient activity. For example, the sensor may detect when a patient is walking, running, climbing, driving, sitting, resting, sleeping, or the like. Sleeping longevity and interruptions to sleep may be very relevant for some indications. In at least some instances, Parkinson's patients have shorter sleep. Also, individuals with overactive bladder or interstitial cystitis have disrupted sleep for urination. Sensing attributes of sleep can be used to adjust one or more stimulation parameters.

The electrical stimulation system 100 can use the measurements from the sensor(s) 107 to modify one or more stimulation parameters. In some embodiments, the modification of stimulation parameters results in steering the electrical stimulation (for example, a stimulation current) to stimulate different portions of the patient tissue or produce a different stimulation field. In some embodiments, this steering can be accomplished by changing the selection of one or more electrodes on the lead used to deliver the electrical stimulation or adjusting the relative amplitudes, frequency, or duration of stimulation from the electrode(s) or any combination thereof. In other embodiments, one or more stimulation parameters can be changed including, but not limited to, amplitude, pulse width, pulse frequency, electrode configuration, electrode polarity, and the like. In at least some embodiments, steering of the electrical stimulation can include multiple timing channels which utilize the electrodes of the lead to generate different electric fields. The electric fields for the different timing channels can be interleaved temporally to alter the electrical stimulation of the patient tissue.

In at least some embodiments, the measurements from the sensor(s) 107 are provided to the processing unit 104. The processing unit 104 includes an algorithm or other computer program that utilizes the sensor measurements and the current stimulation parameters and, optionally, other information regarding the patient, disease or disorder, and the like to determine adjustment to one or more of the stimulation parameters. The processing unit 104 can communicate the adjustment to a clinician or other user or to the external programming unit 106 or control module 102.

In other embodiments, the external programming unit 106 or control module 102 receives the measurements from the sensor(s) 107 and includes an algorithm or other computer program that utilizes the sensor measurements and the current stimulation parameters and, optionally, other information regarding the patient, disease or disorder, and the like to determine adjustment to one or more of the stimulation parameters. In yet other embodiments, the sensor includes the algorithm or other computer program that determines adjustment to one or more of the stimulation parameters based on the sensor measurements.

In addition to the sensor measurements, the algorithm or computer program also receives the current stimulation parameters from, for example, the external programming unit or the control module or any other suitable source. The system can also incorporate one or more of medication information, demographics (for example, age, gender, ethnicity, height, weight, or the like), disease-specific details (for example, pain etiology(ies), number of prior back surgeries, relevant diagnoses, imaging findings, or the like) in the information used to determine adjustments to the stimulation parameters. The algorithm or computer program may determine adjustments based on patient-specific response to previous adjustments, based on population response to previous adjustments, based on patient activity or disease/disorder status determined from the sensor measurements, or any combination thereof. In at least some embodiments, the clinician may direct the patient to perform a particular activity (for example, finger tapping, drawing a spiral or other shape, walking, or the like) and the system uses the sensor measurements during this activity to evaluate and determine adjustments to the stimulation parameters.

In at least some embodiments, the system may utilize a step-wise methodology to altering the stimulation parameters. For example, the system may alter one or more stimulation parameters based on the sensor measurements and then observe the results of the alteration as measured using the sensor (or based on other input such as patient or clinician feedback.) In at least some embodiments, the system waits for a latency period to allow the clinical effect to be measureable by the sensor. For example, for tremor response, the latency period may be less than one minute or five minutes. For blood pressure measurements, the latency period may be five or ten minutes or longer.

In some embodiments, the system may have the objective of improving or optimizing stimulation to produce a desired sensed clinical effect or may improve or co-optimize multiple sensed clinical effects or may improve or co-optimize one or more clinical effects and energy usage. Any suitable algorithmic technique can be used including, but not limited to, brute force parameter space searching, gradient search methods, genetic or stimulated annealing methods, machine learning or support vector machine methods, or the like. Such general techniques for algorithms are known.

In some embodiments, the system may have one or more specific stimulation parameter sets designated for specific patient activities, disease states, or the like. When the system detects the specific patient activity (e.g., walking, running, resting, sleeping, or the like) or disease state using the sensor measurements, the system can set the stimulation parameters to the corresponding set. In some embodiments, the system may also determine a preferred set of stimulation parameters associated with patient activity, disease state, or sensor measurement value or range using the algorithmic techniques described above and may adjust the stimulation parameters to that preferred set upon detecting the patient activity, disease state, or sensor measurement value or range.

Figure 6:
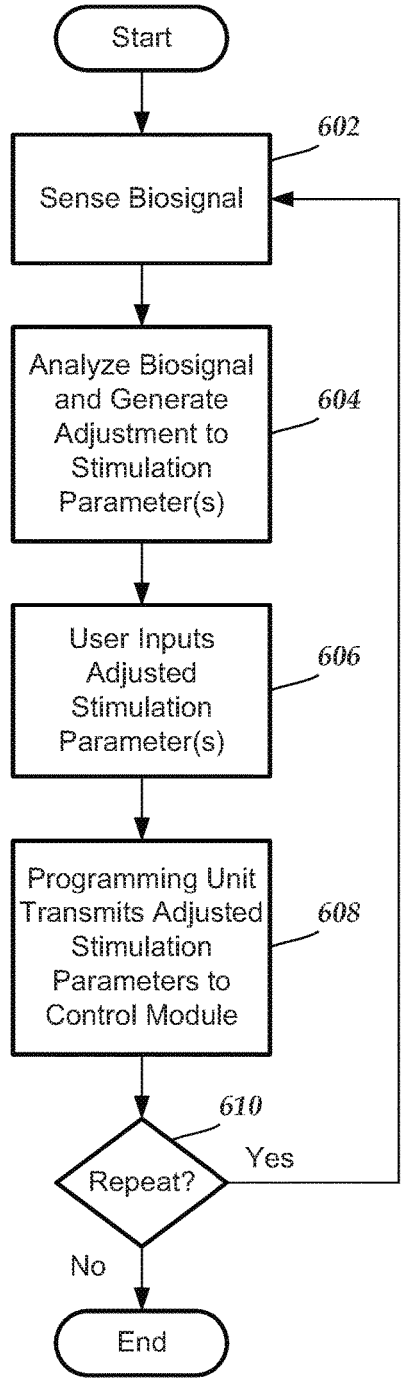
FIG. 6 is a flowchart of one embodiment of a method for adjusting stimulation parameters, according to the invention.

FIG. 6 is a flowchart of one embodiment of a method of adjusting stimulation parameters. In step 602, a biosignal is sensed by one or more sensors. In some embodiments, more than one biosignal can be sensed or biosignals from two or more locations on the body of the patient can be sensed.

In step 604, the biosignal is analyzed and an adjustment to one or more stimulation parameters is generated. Examples of stimulation parameters that can be adjusted include, but are not limited to, pulse frequency, pulse width, electrode field selection (anodes and cathodes which may can also affect the location of stimulation), pulse amplitude, pulse burst frequency or duration, pulse patterns, other pulse timing parameters, and the like. The analysis and generation of the adjustment can be performed by the processing unit 104, external programming unit 106, control module 102, or sensor 107 or any combination thereof. The biosignal can be communicated to the processing unit 104, external programming unit 106, control module 102, or sensor 107 or any combination thereof.

In step 606, a user (such as a clinician or patient) inputs the adjusted stimulation parameter(s) into the external programming unit 106. This process is semi-automated because it includes participation by the user. This participation may be desirable to provide user analysis of the adjusted stimulation parameters. This procedure may be useful, for example, during a control module programming session with a clinician. In such a procedure, the patient may also provide feedback regarding the adjusted stimulation.

In step 608, the external programming unit 106 transmits the adjusted stimulation parameters to the control module 102. The control module 102 then proceeds to deliver electrical stimulation using the adjusted stimulation parameters.

In step, 610, it is determined whether to repeat the process. If so, steps 602-610 are repeated. If not, the method terminates. In some embodiments, the process will automatically repeat without any formal decision to do so. In some embodiments, the process may repeat at regular or irregular intervals.

Figure 7:
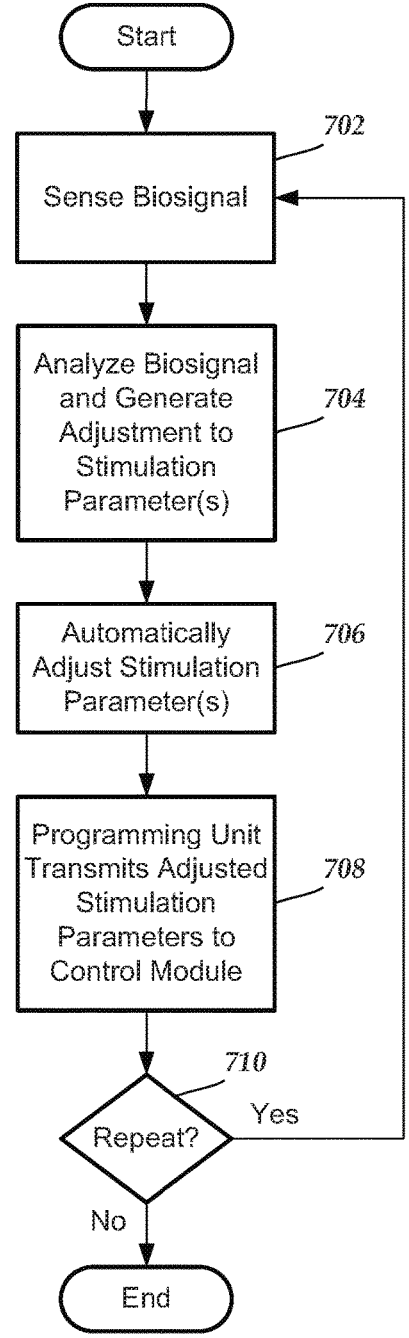
FIG. 7 is a flowchart of one embodiment of a method for testing a range of stimulation parameters, according to the invention.

FIG. 7 is a flowchart of another embodiment of a method of adjusting stimulation parameters. In step 702, a biosignal is sensed by one or more sensors. In some embodiments, more than one biosignal can be sensed or biosignals from two or more locations on the body of the patient can be sensed.

In step 704, the biosignal is analyzed and an adjustment to one or more stimulation parameters is generated. Examples of stimulation parameters that can be adjusted include, but are not limited to, pulse frequency, pulse width, electrode field selection (anodes and cathodes which may can also affect the location of stimulation), pulse amplitude, pulse burst frequency or duration, pulse patterns, other pulse timing parameters, and the like. The analysis and generation of the adjustment can be performed by the processing unit 104, external programming unit 106, control module 102, or sensor 107 or any combination thereof. The biosignal can be communicated to the processing unit 104, external programming unit 106, control module 102, or sensor 107 or any combination thereof.

In step 706, the stimulation parameter(s) are automatically adjusted at the external programming unit 106. In some embodiments, such as during a control module programming session, the external programming unit 106 may optionally display the adjusted parameters so that the clinician or patient can halt the process, if desired, or observe or direct the path of tested parameters.

In step 708, the external programming unit 106 transmits the adjusted stimulation parameters to the control module 102. The control module 102 then proceeds to deliver electrical stimulation using the adjusted stimulation parameters.

In step, 710, it is determined whether to repeat the process. If so, steps 702-710 are repeated. If not, the method terminates. In some embodiments, the process will automatically repeat without any formal decision to do so. In some embodiments, the process may repeat at regular or irregular intervals.

Figure 8:
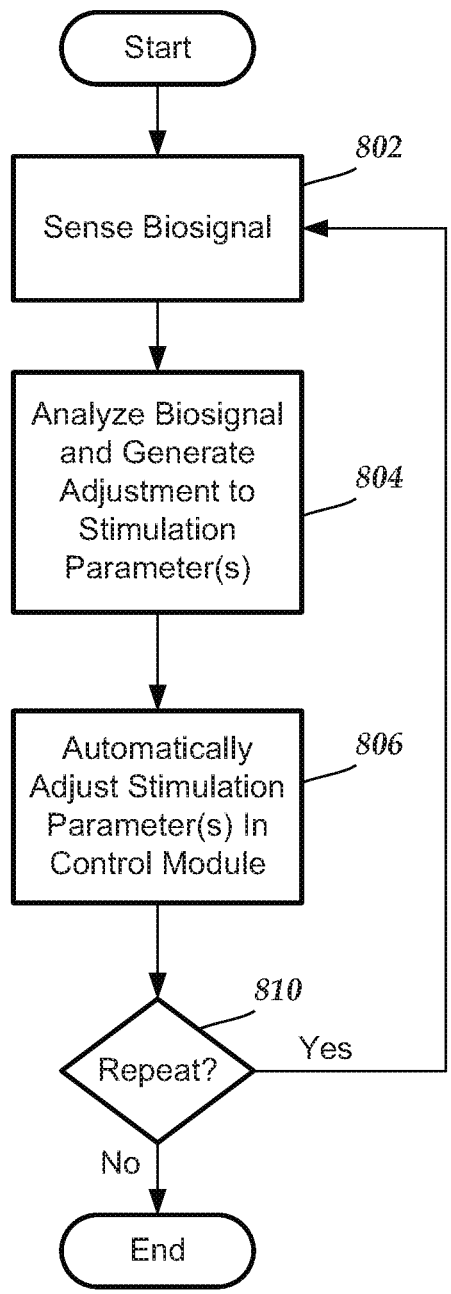
FIG. 8 is a flowchart of one embodiment of a method for requesting patient authorization for using patient data, according to the invention.

FIG. 8 is a flowchart of another embodiment of a method of adjusting stimulation parameters. In step 802, a biosignal is sensed by one or more sensors. In some embodiments, more than one biosignal can be sensed or biosignals from two or more locations on the body of the patient can be sensed.

In step 804, the biosignal is analyzed and an adjustment to one or more stimulation parameters is generated. Examples of stimulation parameters that can be adjusted include, but are not limited to, pulse frequency, pulse width, electrode field selection (anodes and cathodes which may can also affect the location of stimulation), pulse amplitude, pulse burst frequency or duration, pulse patterns, other pulse timing parameters, and the like. The analysis and generation of the adjustment can be performed by the processing unit 104, external programming unit 106, control module 102, or sensor 107 or any combination thereof. The biosignal can be communicated to the processing unit 104, external programming unit 106, control module 102, or sensor 107 or any combination thereof.

In step 806, the stimulation parameters are automatically adjusted in the control module 102. The control module 102 then proceeds to deliver electrical stimulation using the adjusted stimulation parameters. This process may be particularly useful where the control module 102 receives the measurements or the adjustment to the stimulation parameters directly from the sensor 107.

In step, 810, it is determined whether to repeat the process. If so, steps 802-810 are repeated. If not, the method terminates. In some embodiments, the process will automatically repeat without any formal decision to do so. In some embodiments, the process may repeat at regular or irregular intervals.

The processes illustrated in FIGS. 6-8 can be used as a feedback loop to adjust stimulation parameters. The feedback loop may be part of a programming session. Alternatively or additionally, the electrical stimulation system may initiate the feedback loop on a regular or irregular basis or when requested by a user, clinician, or other individual to adjust stimulation parameters.

It will be understood that the system can include one or more of the methods described hereinabove with respect to FIGS. 6-8 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for the control modules, external programming units, sensors, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Figure 9:
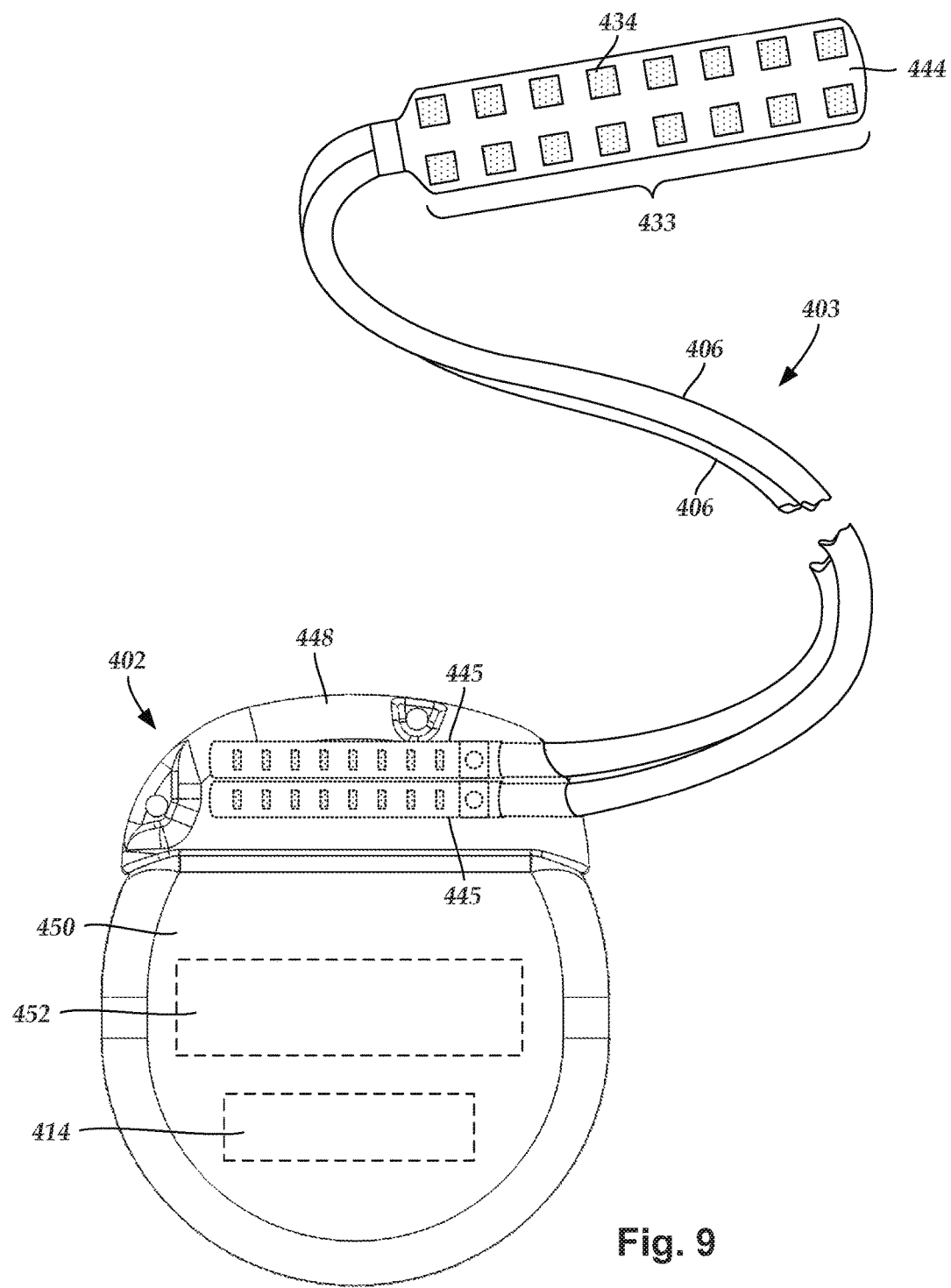
FIG. 9 is a schematic view of one embodiment of an electrical stimulation system that includes a paddle lead electrically coupled to a control module, according to the invention.

FIG. 9 illustrates one embodiment of a control module 402 and lead 403. The lead 403 includes a paddle body 444 and one or more lead bodies 446. In FIG. 9, the lead 403 is shown having two lead bodies 446. It will be understood that the lead 403 can include any suitable number of lead bodies including, for example, one, two, three, four, five, six, seven, eight or more lead bodies 446. An array of electrodes 433, such as electrode 434, is disposed on the paddle body 444, and one or more terminals (e.g., 560 in FIGS. 11A and 11B) are disposed along each of the one or more lead bodies 446. In at least some embodiments, the lead has more electrodes than terminals.

Figure 10:
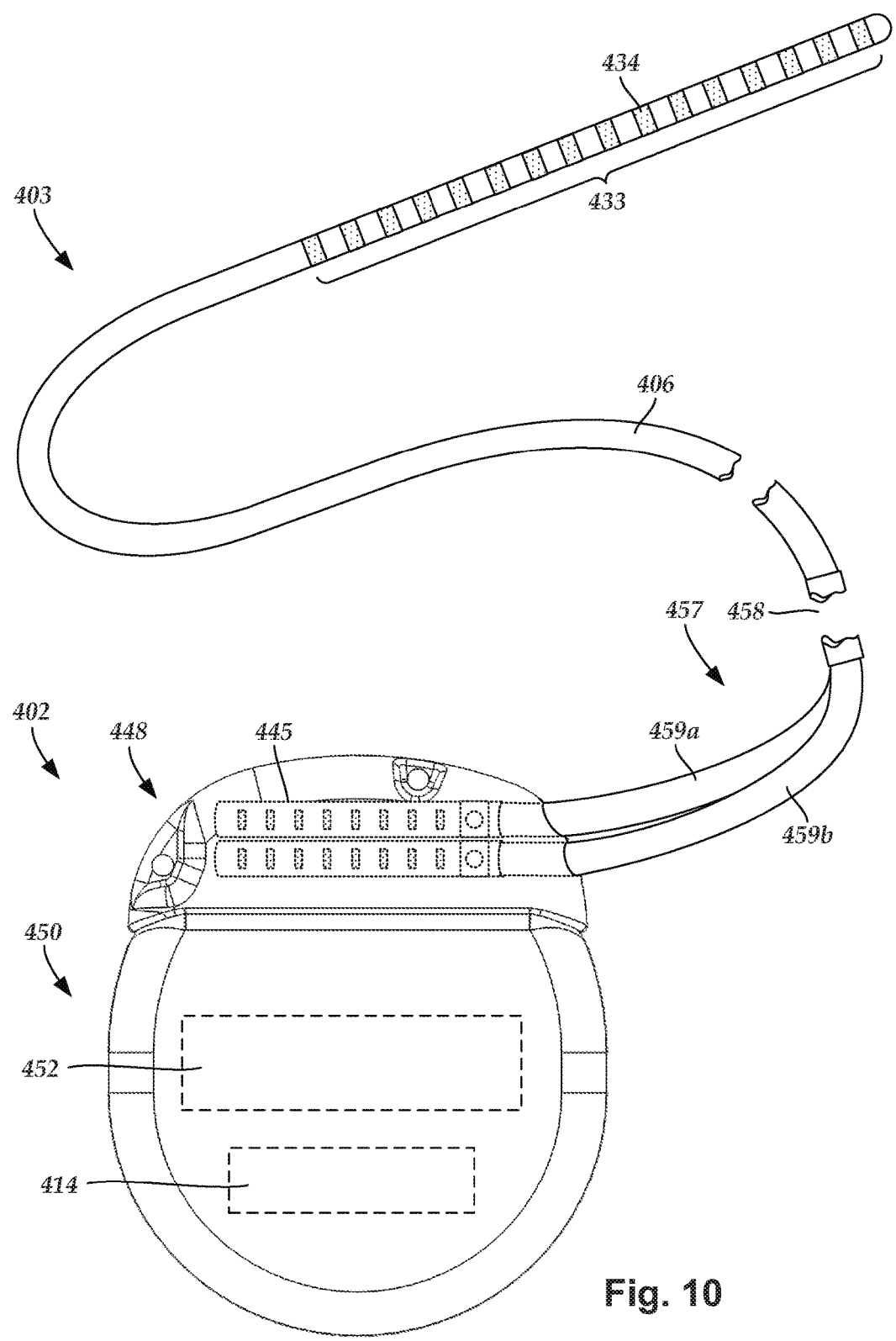
FIG. 10 is a schematic view of one embodiment of an electrical stimulation system that includes a percutaneous lead electrically coupled to a control module, according to the invention.

FIG. 10 illustrates schematically another embodiment in which the lead 403 is a percutaneous lead. In FIG. 10, the electrodes 434 are shown disposed along the one or more lead bodies 446. In at least some embodiments, the lead 403 is isodiametric along a longitudinal length of the lead body 446.

The lead 403 can be coupled to the implantable control module 402 in any suitable manner. In FIG. 9, the lead 403 is shown coupling directly to the implantable control module 402. In at least some other embodiments, the lead 403 couples to the implantable control module 402 via one or more intermediate devices (500 in FIGS. 11A and 11B). For example, in at least some embodiments one or more lead extensions 524 (see e.g., FIG. 11B) can be disposed between the lead 403 and the implantable control module 402 to extend the distance between the lead 403 and the implantable control module 402. Other intermediate devices may be used in addition to, or in lieu of, one or more lead extensions including, for example, a splitter, an adaptor, or the like or combinations thereof. It will be understood that, in the case where the electrical stimulation system includes multiple elongated devices disposed between the lead 403 and the implantable control module 402, the intermediate devices may be configured into any suitable arrangement.

In FIG. 10, the electrical stimulation system 400 is shown having a splitter 457 configured and arranged for facilitating coupling of the lead 403 to the implantable control module 402. The splitter 457 includes a splitter connector 458 configured to couple to a proximal end of the lead 403, and one or more splitter tails 459a and 459b configured and arranged to couple to the implantable control module 402 (or another splitter, a lead extension, an adaptor, or the like).

The implantable control module 402 includes a connector housing 448 and a sealed electronics housing 450. An electronic subassembly 452 (which includes the processor 110 (see, FIGS. 1-3) and the power source 414 are disposed in the electronics housing 450. A connector 445 is disposed in the connector housing 448. The connector 445 is configured and arranged to make an electrical connection between the lead 403 and the electronic subassembly 452 of the implantable control module 402.

The electrical stimulation system or components of the electrical stimulation system, including the paddle body 444, the one or more of the lead bodies 446, and the implantable control module 402, are typically implanted into the body of a patient. The electrical stimulation system can be used for a variety of applications including, but not limited to deep brain stimulation, neural stimulation, spinal cord stimulation, muscle stimulation, and the like.

The electrodes 434 can be formed using any conductive, biocompatible material. Examples of suitable materials include metals, alloys, conductive polymers, conductive carbon, and the like, as well as combinations thereof. In at least some embodiments, one or more of the electrodes 434 are formed from one or more of: platinum, platinum iridium, palladium, palladium rhodium, or titanium.

Any suitable number of electrodes 434 can be disposed on the lead including, for example, four, five, six, seven, eight, nine, ten, eleven, twelve, fourteen, sixteen, twenty-four, thirty-two, or more electrodes 434. In the case of paddle leads, the electrodes 434 can be disposed on the paddle body 444 in any suitable arrangement. In FIG. 9, the electrodes 434 are arranged into two columns, where each column has eight electrodes 434.

The electrodes of the paddle body 444 (or one or more lead bodies 446) are typically disposed in, or separated by, a non-conductive, biocompatible material such as, for example, silicone, polyurethane, polyetheretherketone ("PEEK"), epoxy, and the like or combinations thereof. The one or more lead bodies 446 and, if applicable, the paddle body 444 may be formed in the desired shape by any process including, for example, molding (including injection molding), casting, and the like. The non-conductive material typically extends from the distal ends of the one or more lead bodies 446 to the proximal end of each of the one or more lead bodies 446.

In the case of paddle leads, the non-conductive material typically extends from the paddle body 444 to the proximal end of each of the one or more lead bodies 446. Additionally, the non-conductive, biocompatible material of the paddle body 444 and the one or more lead bodies 446 may be the same or different. Moreover, the paddle body 444 and the one or more lead bodies 446 may be a unitary structure or can be formed as two separate structures that are permanently or detachably coupled together.

Figure 11A:
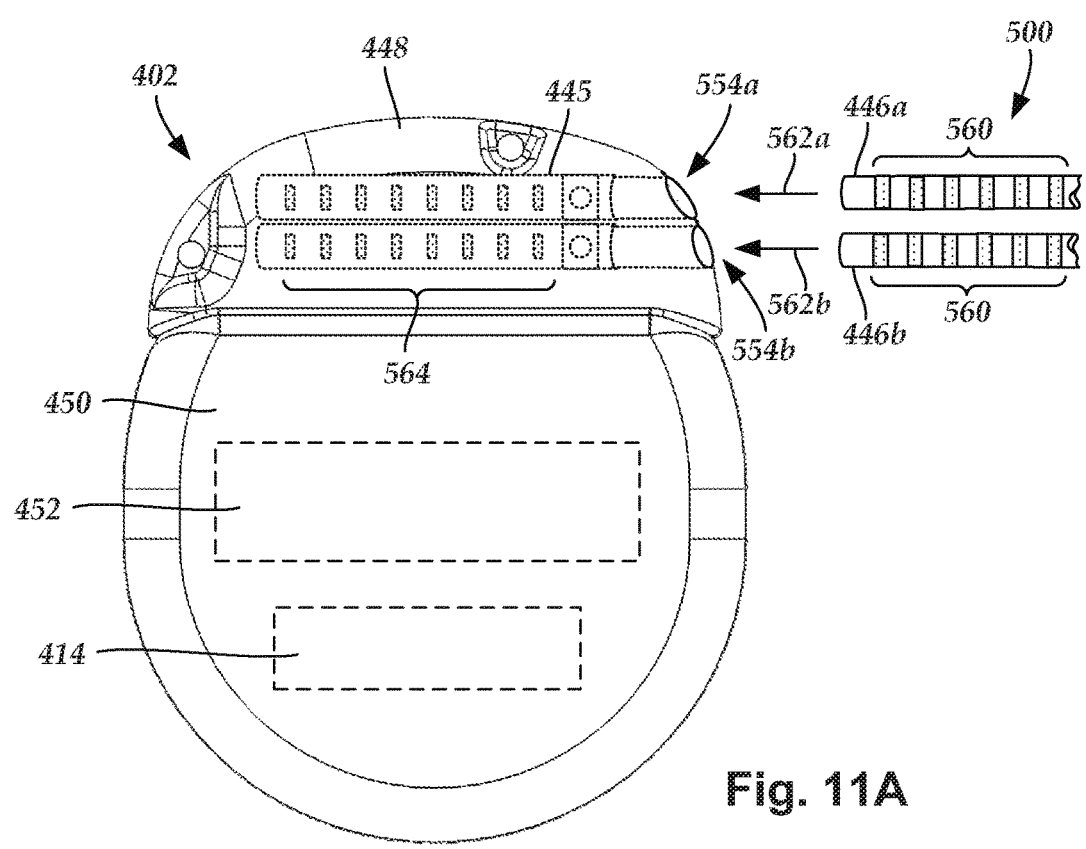
FIG. 11A is a schematic view of one embodiment of the control module of FIG. 9 configured and arranged to electrically couple to an elongated device, according to the invention.
Figure 11B:
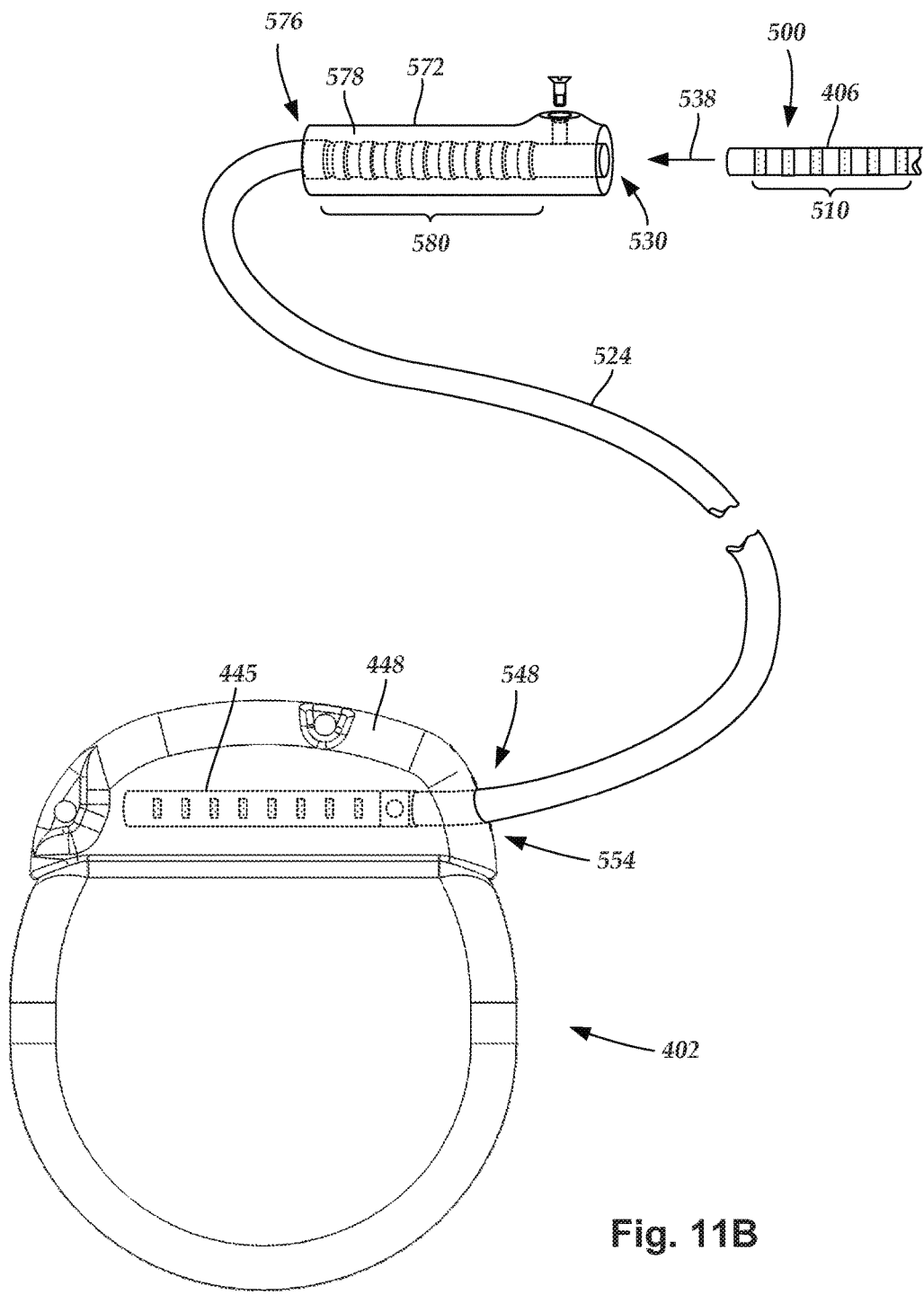
FIG. 11B is a schematic view of one embodiment of a lead extension configured and arranged to electrically couple the elongated device of FIG. 10 to the control module of FIG. 9, according to the invention

One or more terminals (e.g., 560 in FIGS. 11A-11B) are typically disposed along the proximal end of the one or more lead bodies 446 of the electrical stimulation system 400 (as well as any splitters, lead extensions, adaptors, or the like) for electrical connection to corresponding connector contacts (e.g., 564 in FIGS. 11A-11B). The connector contacts are disposed in connectors (e.g., 445 in FIGS. 9-11B; and 572 FIG. 11B) which, in turn, are disposed on, for example, the implantable control module 402 (or a lead extension, a splitter, an adaptor, or the like). One or more electrically conductive wires, cables, or the like (i.e., "conductors"—not shown) extend from the terminal(s) to the electrode(s). In at least some embodiments, there is at least one (or exactly one) terminal conductor for each terminal which extends to at least one (or exactly one) of the electrodes.

The one or more conductors are embedded in the non-conductive material of the lead body 446 or can be disposed in one or more lumens (not shown) extending along the lead body 446. For example, any of the conductors may extend distally along the lead body 446 from the terminals 560.

FIG. 11A is a schematic side view of one embodiment of a proximal end of one or more elongated devices 500 configured and arranged for coupling to one embodiment of the connector 445. The one or more elongated devices may include, for example, one or more of the lead bodies 446 of FIG. 9, one or more intermediate devices (e.g., a splitter, the lead extension 524 of FIG. 11B, an adaptor, or the like or combinations thereof), or a combination thereof.

The connector 445 defines at least one port into which a proximal ends 446A, 446B of the elongated device 500 can be inserted, as shown by directional arrows 562a, 562b. In FIG. 11A (and in other figures), the connector housing 448 is shown having two ports 554a, 554b. The connector housing 448 can define any suitable number of ports including, for example, one, two, three, four, five, six, seven, eight, or more ports.

The connector 445 also includes one or more connector contacts, such as connector contact 564, disposed within each port 554a, 554b. When the elongated device 500 is inserted into the ports 554a, 554b, the connector contact(s) 564 can be aligned with the terminal(s) 560 disposed along the proximal end(s) of the elongated device(s) 500 to electrically couple the implantable control module 402 to the electrodes (434 of FIG. 9) disposed on the paddle body 445 of the lead 403. Examples of connectors in implantable control modules are found in, for example, U.S. Pat. Nos. 7,244,150 and 8,224,450, which are incorporated by reference.

FIG. 11B is a schematic side view of another embodiment that includes a lead extension 524 that is configured and arranged to couple one or more elongated devices 500 (e.g., one of the lead bodies 446 of FIGS. 9 and 10, the splitter 457 of FIG. 10, an adaptor, another lead extension, or the like or combinations thereof) to the implantable control module 402. In FIG. 11B, the lead extension 524 is shown coupled to a single port 554 defined in the connector 445. Additionally, the lead extension 524 is shown configured and arranged to couple to a single elongated device 500. In alternate embodiments, the lead extension 524 is configured and arranged to couple to multiple ports 554 defined in the connector 445, or to receive multiple elongated devices 500, or both.

A lead extension connector 572 is disposed on the lead extension 524. In FIG. 11B, the lead extension connector 572 is shown disposed at a distal end 576 of the lead extension 524. The lead extension connector 572 includes a connector housing 578. The connector housing 578 defines at least one port 530 into which terminal(s) 560 of the elongated device 500 can be inserted, as shown by directional arrow 538. The connector housing 578 also includes a plurality of connector contacts, such as connector contact 580. When the elongated device 500 is inserted into the port 530, the connector contacts 580 disposed in the connector housing 578 can be aligned with the terminal(s) 560 of the elongated device 500 to electrically couple the lead extension 524 to the electrodes (434 of FIGS. 9 and 10) disposed along the lead (403 in FIGS. 9 and 10).

In at least some embodiments, the proximal end of the lead extension 524 is similarly configured and arranged as a proximal end of the lead 403 (or other elongated device 500). The lead extension 524 may include one or more electrically conductive wires (not shown) that electrically couple the connector contact(s) 580 to a proximal end 548 of the lead extension 524 that is opposite to the distal end 576. The conductive wire(s) disposed in the lead extension 524 can be electrically coupled to one or more terminals (not shown) disposed along the proximal end 548 of the lead extension 524. The proximal end 548 of the lead extension 524 is configured and arranged for insertion into a connector disposed in another lead extension (or another intermediate device). As shown in FIG. 11B, the proximal end 548 of the lead extension 524 is configured and arranged for insertion into the connector 445.

The embodiments of FIGS. 9-11B illustrate a control module 402 with a connector 445 into which a proximal end portion of the lead or lead extension can be removably inserted. It will be recognized, however, that other embodiments of a control module and lead can have the lead or lead extension permanently attached to the control module. Such an arrangement can reduce the size of the control module as the conductors in the lead can be permanently attached to the electronic subassembly. It will also be recognized that, in at least some embodiments, more than one lead can be attached to a control module.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
    an implantable control module configured for implantation in a body of a patient and comprising an antenna and a processor coupled to the antenna, wherein the implantable control module is configured to provide electrical stimulation signals to an electrical stimulation lead coupled to the implantable control module for stimulation of patient tissue;
    an external programming unit configured to communicate with the processor of the implantable control module using the antenna and to provide or update stimulation parameters for production of the electrical stimulation signals;
    a sensor configured to be disposed on or within the body of the patient and to measure a biosignal indicative of muscle tremor or rigidity; and
    a biosignal processor configured to communicate with the sensor to receive the biosignal, to determine a disease/disorder status from the muscle tremor or rigidity indicated by the biosignal, and to generate an adjustment to one or more of the stimulation parameters based on the determined disease/disorder status and the biosignal, wherein the adjustment is configured to steer the electrical stimulation signals to stimulate a region of the patient tissue that is different, at least in part, from a region of the patient tissue stimulated prior to the adjustment.

2. The electrical stimulation system of claim 1, wherein the external programming unit comprises the biosignal processor.

3. The electrical stimulation system of claim 1, wherein the biosignal processor is configured for communication with the external programming unit to deliver the adjustment to the external programming unit.

4. The electrical stimulation system of claim 1, wherein the biosignal processor is configured to deliver the adjustment to at least one of the external programming unit or the control module.

5. The electrical stimulation system of claim 1, further comprising a lead coupleable to the control module and comprising a plurality of electrodes for delivering the electrical stimulation signals to the patient tissue.

6. The electrical stimulation system of claim 5, wherein the sensor is disposed on the lead.

7. The electrical stimulation system of claim 1, wherein the sensor is disposed on the control module.

8. The electrical stimulation system of claim 1, wherein the adjustment is provided to the control module automatically and without user intervention.

9. The electrical stimulation system of claim 1, wherein the biosignal processor is configured to generate the adjustment based, at least in part, on medication information.

10. The electrical stimulation system of claim 1, wherein the sensor comprises a global positioning sensor.

11. An electrical stimulation system, comprising:
an implantable control module configured for implantation in a body of a patient and comprising an antenna and a processor coupled to the antenna, wherein the implantable control module is configured to provide electrical stimulation signals to an electrical stimulation lead coupled to the implantable control module for stimulation of patient tissue;
an external programming unit configured to communicate with the processor of the implantable control module using the antenna and to provide or update stimulation parameters for production of the electrical stimulation signals;
a sensor configured to be disposed on or within the body of the patient and to measure a biosignal; and
a biosignal processor configured to communicate with the sensor to receive the biosignal and to generate an adjustment to one or more of the stimulation parameters based on the biosignal, wherein the adjustment is configured to steer the electrical stimulation signals to stimulate a region of the patient tissue that is different, at least in part, from a region of the patient tissue stimulated prior to the adjustment, wherein the biosignal processor is configured so that when the biosignal is indicative of a disease or disorder status, the adjustment is followed by the biosignal processor waiting for a predetermined latency period after which the biosignal processor is configured to communicate with the sensor to observe a result of the adjustment using the biosignal and determine whether to provide a further adjustment of the stimulation parameters to improve the stimulation.

12. The electrical stimulation system of claim 11, wherein, subsequent to the predetermined latency period, the biosignal processor directs the patient to perform a predetermined activity.

13. An electrical stimulation system, comprising:
a sensor configured to be disposed on or within the body of the patient and to measure a biosignal indicative of muscle tremor or rigidity; and
a control module comprising a processor, wherein the control module is configured to use stimulation parameters to provide electrical stimulation signals to an electrical stimulation lead coupled to the control module for stimulation of patient tissue, wherein the processor is configured to communicate with the sensor to receive the biosignal, to determine a disease/disorder status from the muscle tremor or rigidity indicated by the biosignal and to generate an adjustment to one or more of the stimulation parameters based on the determined/disorder status and the biosignal, wherein the adjustment is configured to steer the electrical stimulation signals to stimulate a region of the patient tissue that is different, at least in part, from a region of the patient tissue stimulated prior to the adjustment.

14. The electrical stimulation system of claim 13, wherein the control module is an implantable control module configured and arranged for implantation in a body of a patient, the implantable control module further comprising an antenna coupled to the processor.

15. The electrical stimulation system of claim 13, further comprising a lead coupleable to the control module and comprising a plurality of electrodes for delivering the electrical stimulation signals to the patient tissue.

16. The electrical stimulation system aim 15, wherein the sensor is disposed on the lead.

17. The electrical stimulation system of claim 13, wherein the sensor is disposed on the control module.

18. The electrical stimulation system of claim 13, wherein the processor is configured so that the adjustment is followed by the processor waiting for a predetermined latency period after which the processor is configured to communicate with the sensor to observe a result of the adjustment using the biosignal and determine whether to provide a further adjustment of the stimulation parameters to improve the stimulation.

19. A method of providing electrical stimulation to a patient using the electrical stimulation system of claim 1, the method comprising
measuring a biosignal indicative of muscle tremor or rigidity using the sensor;
determining a disease/disorder status from the muscle tremor or rigidity indicated by the biosignal;
generating an adjustment to one or more of the stimulation parameters based on the determined disease/disorder status;
communicating the adjustment to the implantable control module implanted in the patient; and
delivering electrical stimulation to the patient using the adjustment to the one or more of the stimulation parameters.

20. A method of providing electrical stimulation to a patient using the electrical stimulation system of claim 11, the method comprising
measuring a biosignal using the sensor;
generating an adjustment to one or more of the stimulation parameters based on the biosignal;
communicating the adjustment to the implantable control module implanted in the patient;
delivering electrical stimulation to the patient using the adjustment to the one or more of the stimulation parameters;

when the biosignal is indicative of a disease or disorder status, waiting for the predetermined latency period;
observing, by the sensor, a result of the adjustment using the biosignal; and
determining whether to provide a further adjustment of the stimulation parameters to improve the stimulation.

\* \* \* \* \*